US00PP23807P2

(12) United States Plant Patent
Dümmen

(10) Patent No.: US PP23,807 P2
(45) Date of Patent: Aug. 6, 2013

(54) ***PELARGONIUM* PLANT NAMED 'DUESALSAPI'**

(50) Latin Name: *Pelargonium zonale×Pelargonium peltatum*
Varietal Denomination: Duesalsapi

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 58 days.

(21) Appl. No.: 13/373,726

(22) Filed: Nov. 28, 2011

(51) Int. Cl.
*A01H 5/00* (2006.01)

(52) U.S. Cl.
USPC ..... Plt./324

(58) Field of Classification Search
USPC ..... Plt./324
See application file for complete search history.

*Primary Examiner* — Annette Para
(74) *Attorney, Agent, or Firm* — C. A. Whealy

(57) ABSTRACT

A new and distinct cultivar of interspecific Geranium plant named 'Duesalsapi', characterized by its compact, semi-upright to outwardly spreading plant habit; moderately vigorous growth habit; freely basal branching habit; freely flowering habit; large light red purple-colored semi-double flowers; and good garden performance.

1 Drawing Sheet

Botanical designation: *Pelargonium zonale×Pelargonium peltatum.*
Cultivar denomination: 'DUESALSAPI'.

CROSS REFERENCED TO CLOSELY-RELATED APPLICATIONS

Title: *Pelargonium* Plant Named 'DUESALSADAR'
Applicant: Tobias Dümmen
Filed: Concurrently with this application

BACKGROUND OF THE INVENTION

The present invention relates to a new and distinct cultivar of interspecific Geranium plant, botanically known as *Pelargonium zonale×Pelargonium peltatum* and hereinafter referred to by the name 'Duesalsapi'.

The new interspecific Geranium plant is a product of a planned breeding program conducted by the Inventor in Rheinberg, Germany. The objective of the breeding program is to create new freely-branching interspecific Geranium plants with semi-upright growth habit and large attractive flowers.

The new interspecific Geranium plant originated from a cross-pollination made by the Inventor in July, 2009 in Rheinberg, Germany of a proprietary selection of *Pelargonium zonale×Pelargonium peltatum* identified as code number F-03-04-18, not patented, as the female, or seed, parent with a proprietary selection of *Pelargonium zonale×Pelargonium peltatum* identified as code number Z04-0808-004, not patented, as the male, or pollen, parent. The new interspecific Geranium plant was discovered and selected by the Inventor as a single flowering plant from within the progeny of the stated cross-pollination in a controlled greenhouse environment in Rheinberg, Germany in May, 2010.

Asexual reproduction of the new interspecific Geranium plant by vegetative terminal cuttings in a controlled greenhouse environment in Rheinberg, Germany since June, 2010 has shown that the unique features of this new interspecific Geranium plant are stable and reproduced true to type in successive generations.

SUMMARY OF THE INVENTION

Plants of the new interspecific Geranium have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Duesalsapi'. These characteristics in combination distinguish 'Duesalsapi' as a new and distinct interspecific Geranium plant:

1. Compact, semi-upright to outwardly spreading plant habit.
2. Moderately vigorous growth habit.
3. Freely basal branching habit.
4. Freely flowering habit.
5. Large light red purple-colored semi-double flowers.
6. Good garden performance.

Plants of the new interspecific Geranium differ primarily from plants of the female parent selection in the following characteristics:

1. Plants of the new interspecific Geranium are more vigorous than plants of the female parent selection.
2. Plants of the new interspecific Geranium have darker green-colored leaves than plants of the female parent selection.
3. Plants of the new interspecific Geranium and the female parent selection differ in flower color as plants of the female parent selection have dark red-colored flowers.

Plants of the new interspecific Geranium differ primarily from plants of the male parent selection in the following characteristics:

1. Plants of the new interspecific Geranium are not as upright as plants of the male parent selection.

2. Plants of the new interspecific Geranium have darker green-colored leaves than plants of the male parent selection.

Plants of the new interspecific Geranium can be compared to plants of the interspecific Geranium 'Duesalsadar', disclosed in a U.S. Plant patent application Ser. No. 13/373,742. Plants of the new interspecific Geranium and 'Duesalsadar' differ primarily in flower color as plants of 'Duesalsadar' have red-colored flowers. In addition, plants of the new interspecific Geranium have semi-double flowers whereas plants of 'Duesalsadar' have single flowers.

Plants of the new interspecific Geranium can be compared to plants of interspecific Geranium 'Cante Ros', disclosed in U.S. Plant Pat. No. 15,834. In side-by-side comparisons conducted in Rheinberg, Germany, plants of the new interspecific Geranium differed primarily from plants of 'Cante Ros' in the following characteristics:

1. Plants of the new interspecific Geranium were more vigorous than plants of 'Cante Ros'.
2. Plants of the new interspecific Geranium had larger leaves than plants of 'Cante Ros'.
3. Plants of the new interspecific Geranium had larger inflorescences than plants of 'Cante Ros'.
4. Plants of the new interspecific Geranium and 'Cante Ros' differed in flower color.

BRIEF DESCRIPTION OF THE PHOTOGRAPH

The accompanying colored photograph illustrates the overall appearance of the new interspecific Geranium plant showing the colors as true as it is reasonably possible to obtain in colored reproductions of this type. Colors in the photograph may differ slightly from the color values cited in the detailed botanical description which accurately describe the colors of the new interspecific Geranium plant. The photograph comprises a side perspective view of a typical flowering plant of 'Duesalsapi' grown in a container.

DETAILED BOTANICAL DESCRIPTION

The aforementioned photograph and following observations and measurements describe plants grown during the summer in 12-cm containers in a glass-covered greenhouse in Rheinberg, Germany and under cultural practices which closely approximate commercial *Pelargonium* production. During the production of the plants, day and night temperatures averaged 18° C. and light levels averaged 4,500 lux. Plants were pinched one time three weeks after planting and were 13 weeks old when the photograph and the description were taken. In the detailed description, color references are made to The Royal Horticultural Society Colour Chart, 1995 Edition, except where general terms of ordinary dictionary significance are used.

Botanical classification: *Pelargonium zonale*×*Pelargonium peltatum* 'Duesalsapi'.

Parentage:

*Female, or seed, parent*.—Proprietary selection of *Pelargonium zonale*×*Pelargonium peltatum* identified as code number F-03-04-18, not patented.

*Male or pollen parent*.—Proprietary selection of *Pelargonium zonale*×*Pelargonium peltatum* identified as code number Z04-0808-004, not patented.

Propagation:

*Type*.—By vegetative terminal cuttings.

*Time to initiate roots, summer*.—About five days at temperatures of about 20° C.

*Time to initiate roots, winter*.—About seven days at temperatures of about 20° C.

*Time to produce a rooted young plant, summer*.—About three weeks at temperatures of about 20° C.

*Time to produce a rooted young plant, winter*.—About four weeks at temperatures of about 20° C.

*Root description*.—Fine, fibrous; white in color.

*Rooting habit*.—Freely branching; dense.

Plant description:

*General appearance*.—Compact, semi-upright to outwardly spreading plant habit; uniformly rounded; densely foliated.

*Growth and branching habit*.—Moderately vigorous growth habit; freely basal branching habit with about three basal branches developing per plant.

*Plant height to top of flower umbels*.—About 26.5 cm.

*Plant height to top of foliar plane*.—About 12.5 cm.

*Plant width*.—About 27 cm.

*Lateral branches*.—Length: About 28 cm. Diameter: About 7 mm. Internode length: About 2.7 cm. Texture: Pubescent. Strength: Moderately strong. Color: Close to 144B.

Foliage description:

*Arrangement*.—Alternate; simple.

*Length*.—About 8 cm.

*Width*.—About 9 cm.

*Shape*.—Reniform.

*Apex*.—Acute.

*Base*.—Cordate.

*Margin*.—Crenate.

*Venation pattern*.—Palmate.

*Texture, upper surface*.—Pubescent.

*Texture, lower surface*.—Smooth, glabrous.

*Color*.—Developing leaves, upper surface: Close to 137A. Developing leaves, lower surface: Close to 146A. Fully expanded leaves, upper surface: Close to 147A; venation, close to 147B. Fully expanded leaves, lower surface: Close to 146A; venation, close to 146C. Zonation pattern: Not discernible.

*Petiole*.—Length: About 6.8 cm. Diameter: About 3 mm. Texture, upper and lower surfaces: Smooth, glabrous. Color, upper surface: Close to 146A. Color, lower surface: Close to 144A.

Flower description:

*Flower arrangement*.—Semi-double rotate flowers arranged in rounded hemispherical umbels arising from apical leaf axils; umbels displayed above the foliage on moderately strong peduncles; flowers face mostly upright.

*Fragrance*.—None detected.

*Quantity of flowers*.—Freely flowering habit, about 26 flowers per umbel.

*Flowering season*.—Year-round under greenhouse conditions; in outdoor nurseries and gardens in Germany, flowering is continuous from spring throughout the summer; plants begin to flower about eight weeks after planting.

*Flower longevity*.—Individual flowers last about five to seven days on the plant; flowers persistent.

*Umbel height*.—About 5.5 cm.

*Umbel diameter*.—About 11 cm.

*Flower diameter*.—About 5.3 cm by 4.3 cm.

*Flower depth (height)*.—About 2 cm.

*Flower buds*.—Length: About 1 cm. Diameter: About 5 mm. Shape: Ovoid. Color: Close to 57A.

*Petals*.—Quantity per flower: Five, arranged in a single whorl. Length: About 2.1 cm. Width: About 1.8 cm. Shape: Obovate. Apex: Rounded. Base: Attenuate. Margin: Sinuate. Texture, upper and lower surfaces: Smooth, glabrous. Color: When opening, upper surface: Close to 66A. When opening, lower surface: Close to 67C. Fully opened, upper surface: Close to 64C; color becoming closer to 61B with development. When opening, lower surface: Close to 68B; color becoming closer to 61B with development.

*Petaloids*.—Quantity per flower: Two. Length: About 2.5 cm. Width: About 1.6 cm. Shape: Obovate. Apex: Rounded. Base: Attenuate. Margin: Sinuate. Texture, upper and lower surfaces: Smooth, glabrous. Color: When opening, upper surface: Close to 66A. When opening, lower surface: Close to 67C. Fully opened, upper surface: Close to 64C. When opening, lower surface: Close to 68B.

*Sepals*.—Quantity per flower: Five, arranged in a single whorl. Length: About 1.1 cm. Width: About 3 mm. Shape: Ensiform. Apex: Apiculate. Base: Attenuate. Margin: Entire. Color, upper and lower surfaces: Close to 146A.

*Peduncle* (*umbel stem*).—Length: About 11 cm. Diameter: About 3 mm. Strength: Moderately strong. Texture: Smooth, glabrous. Color: Close to 144A.

*Pedicel* (*individual flower stem*).—Length: About 3.9 cm. Diameter: About 1.5 mm. Strength: Moderately strong. Texture: Smooth, glabrous. Color: Close to 144B tinted with close to 178A.

*Reproductive organs*.—Androecium: Stamen quantity per flower: About six to seven. Filament length: About 6.7 mm. Filament color: Close to 62A and 67A. Anther length: About 2.8 mm. Anther shape: Oval. Anther color: Close to 61A. Pollen amount: Moderate. Pollen color: Close to 28A. Gynoecium: Pistil quantity per flower: One. Pistil length: About 6 mm. Stigma shape: Parted. Stigma color: Close to 60B. Style length: About 2 mm. Style color: Close to 60B. Ovary color: Close to 146B.

*Seeds and fruits*.—Seed and fruit development have not been observed on plants of the new interspecific Geranium.

Disease & pest resistance: Plants of the new interspecific Geranium have not been observed to be resistant to pathogens and pests common to interspecific Geraniums.

Garden performance: Plants of the new interspecific Geranium have been observed have good garden performance and to tolerate rain, wind, and temperatures ranging from about 5° C. to about 40° C.

It is claimed:

1. A new and distinct interspecific Geranium plant named 'Duesalsapi' as illustrated and described.

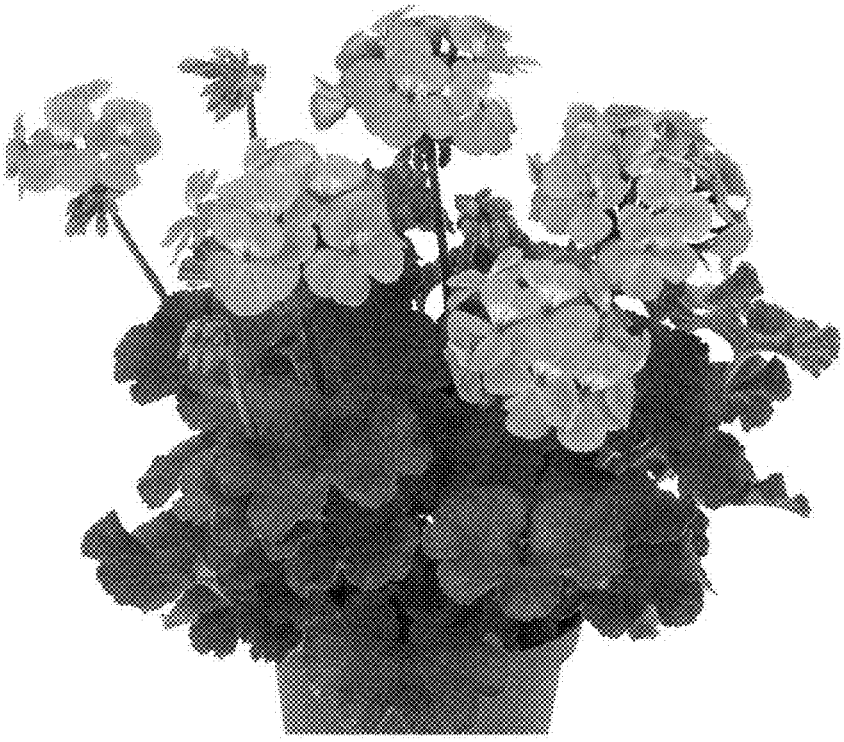

* * * * *